(12) United States Patent
Wang et al.

(10) Patent No.: US 11,857,357 B2
(45) Date of Patent: Jan. 2, 2024

(54) IMAGING SYSTEMS AND METHODS

(71) Applicant: SHANGHAI UNITED IMAGING HEALTHCARE CO., LTD., Shanghai (CN)

(72) Inventors: Wenying Wang, Houston, TX (US); Tao Feng, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 30 days.

(21) Appl. No.: 17/446,969

(22) Filed: Sep. 5, 2021

(65) Prior Publication Data
US 2023/0072958 A1    Mar. 9, 2023

(51) Int. Cl.
*G01T 1/164* (2006.01)
*A61B 6/03* (2006.01)
*A61B 6/00* (2006.01)

(52) U.S. Cl.
CPC ............ *A61B 6/5235* (2013.01); *A61B 6/037* (2013.01); *G01T 1/1642* (2013.01)

(58) Field of Classification Search
CPC ............................... A61B 6/037; A61B 6/5235
See application file for complete search history.

(56) References Cited

U.S. PATENT DOCUMENTS

| | | | | |
|---|---|---|---|---|
| 5,512,754 A * | 4/1996 | Enos | ...................... | G21K 1/025 250/363.1 |
| 5,638,817 A * | 6/1997 | Morgan | ................ | G01T 1/1615 250/363.1 |
| 8,884,235 B2 * | 11/2014 | Heukensfeldt Jansen | ................... | G21K 1/025 378/150 |
| 2007/0183642 A1 * | 8/2007 | Ye | ........................ | G06T 11/006 382/131 |
| 2012/0305812 A1 * | 12/2012 | Bowen | .................. | G01T 1/1611 250/505.1 |

OTHER PUBLICATIONS

Sayed et al. Effects of Unconventional (Material) Filters on the Quality of Images Produced by Three Gamma Camera Systems in Tc-99m SPECT, International Journal of Healthcare Sciences vol. 4, No. 1, pp. 203-209 (Year: 2016).*

* cited by examiner

*Primary Examiner* — David P Porta
*Assistant Examiner* — Jeremy S Valentiner
(74) *Attorney, Agent, or Firm* — METIS IP LLC

(57) ABSTRACT

The present disclosure provides an imaging system and method for nuclear medicine imaging. The imaging system may include a detector and a collimator. The detector may be configured to detect photons. The collimator may have at least two sets of pinholes. The at least two sets of pinholes may include a first set of first pinholes and a second set of second pinholes. Each second pinhole of the second set of second pinholes may be equipped with a filter configured to filter the photons.

20 Claims, 10 Drawing Sheets

800

| Obtaining a first projection data set associated with a first portion of photons each of which having a first energy, and a second projection data set associated with a second portion of photons each of which having a second energy | ~810 |

↓

| Generating an image based on the first projection data set and the second projection data set | ~820 |

FIG. 8

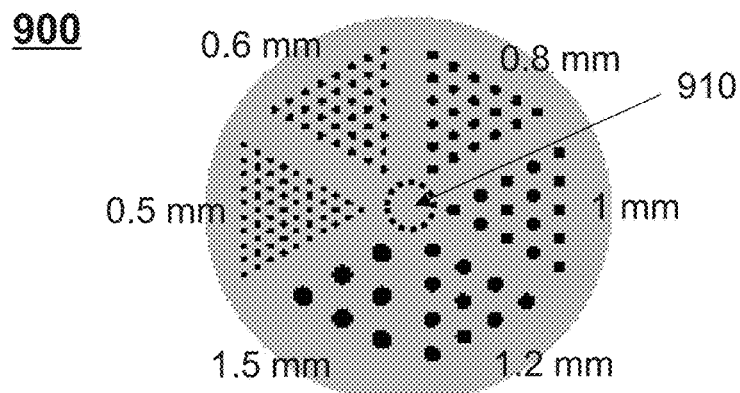
FIG. 9A
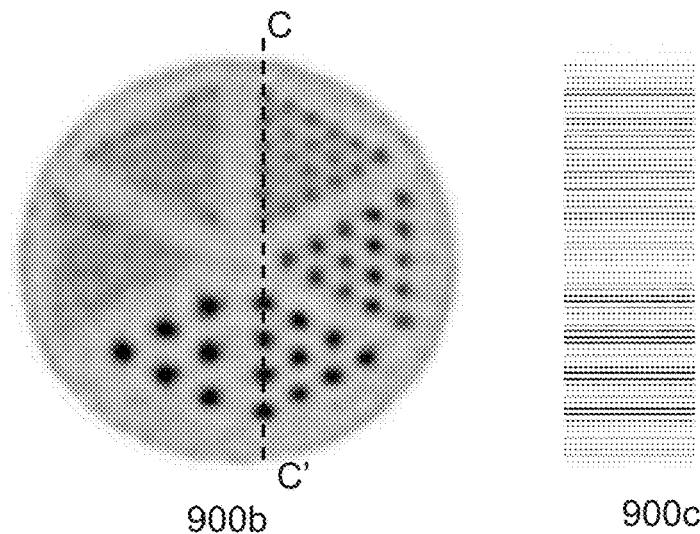
900b
FIG. 9B
900c
FIG. 9C
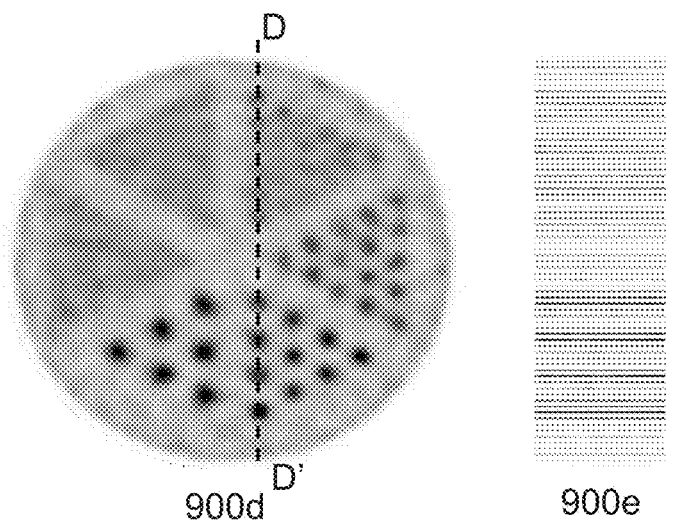
900d
FIG. 9D
900e
FIG. 9E

IMAGING SYSTEMS AND METHODS

TECHNICAL FIELD

The disclosure generally relates to the field of imaging, and more particularly relates to imaging systems and methods using a collimator having multi-pinholes equipped with filters.

BACKGROUND

Single-photon emission computed tomography (SPECT), positron emission tomography (PET), etc., are nuclear medicine functional imaging techniques widely used in medical diagnosis. For example, SPECT images may be indicative of some physiological parameters of tracer kinetics and can aid the evaluation of the physiology (or functionality) and/or anatomy (or structure) of a target organ or tissue, as well as its biochemical properties. Generally, the sensitivity of a nuclear medicine imaging device may be relatively low, or an image generated based thereon may have artifacts due to a low utilization rate (e.g., about 1%) of photons in imaging. Therefore, it is desirable to provide systems and methods for imaging with improved sensitivity and accuracy.

SUMMARY

According to an aspect of the present disclosure, a SPECT system is provided. The SPECT system may include a detector configured to detect photons and a collimator having at least two sets of pinholes. The at least two sets of pinholes may include a first set of first pinholes and a second set of second pinholes. Each second pinhole of the second set of second pinholes may be equipped with a filter configured to filter the photons.

In some embodiments, the first set of first pinholes may be patterned such that first projections of a field of view (FOV) of the SPECT system through the first set of first pinholes onto the detector have no overlapping region. The second set of second pinholes may be patterned such that second projections of the FOV of the SPECT system through the second set of second pinholes onto the detector have no overlapping region. At least one of the first projections may be overlapped with at least one of the second projections.

In some embodiments, at least one of the first projections may be overlapped with at least two of the second projections or at least one of the second projections is overlapped with at least two of the first projections.

In some embodiments, the second set of second pinholes may interleave between the first set of first pinholes.

In some embodiments, the first set of first pinholes may include a first count of rows of first pinholes and the second set of second pinholes may include a second count of rows of second pinholes. The second count may be less than the first count.

In some embodiments, at least one second pinhole of the second set of pinholes may be arranged at a center of a region encompassing four first pinholes adjacent to the at least one second pinhole.

In some embodiments, the collimator may be ring shaped. Each row of first pinholes may be arranged on a plane perpendicular to a central axis of the collimator. Each row of second pinholes may be arranged on a plane perpendicular to the central axis of the collimator. The detector may be ring shaped and be concentric with the collimator.

In some embodiments, each row of first pinholes may be equally spaced and each row of second pinholes may be equally spaced.

In some embodiments, spacings between the each row of first pinholes may be equal to spacings between the each row of second pinholes.

In some embodiments, the photons may be emitted from an object with a radioactive tracer. The radioactive tracer may have at least two characteristic peaks.

In some embodiments, the detector may be configured for multiplex detection of a first portion of the photons each of which having a first energy, and a second portion of the photons each of which having a second energy. The first energy and the second energy may correspond to two of the at least two characteristic peaks, respectively.

In some embodiments, the photons detected by the detector may include a first count of photons that pass through the first set of first pinholes, and a second count of photons that pass through the second set of second pinholes. The first count of photons may include a plurality of first photons each of which having the first energy and a plurality of second photons each of which having the second energy. The second count of photons may include a plurality of third photons each of which having the first energy and a plurality of fourth photons each of which having the second energy. A first ratio of a count of the first photons to a count of the second photons may be different from a second ratio of a count of the third photons to a count of the fourth photons.

In some embodiments, the radioactive tracer may include at least one of indium-111, or iodine-131.

In some embodiments, the filter may include a heavy metal sheet.

In some embodiments, the heavy metal sheet may include at least one of a tungsten sheet, a gold sheet, a copper sheet, or a lead sheet.

In some embodiments, the filter may have a thickness in a range from 0.01 mm to 1 mm.

In some embodiments, the collimator may further include a cover plate configured to adjustably cover the second set of second pinholes.

In some embodiments, each first pinhole of the first set of first pinholes may be equipped with a filter different from the filter that equipped on each second pinhole of the second set of second pinholes.

According to another aspect of the present disclosure, a system is provided. The system may include at least one storage device storing executable instructions for single-photon emission computed tomography (SPECT) imaging, and at least one processor in communication with the at least one storage device. When executing the executable instructions, the at least one processor may cause the system to perform one or more of the following operations. The system may obtain a first projection data set associated with a first portion of photons each of which having a first energy, and a second projection data set associated with a second portion of photons each of which having a second energy. The system may further generate an image based on the first projection data set and the second projection data set.

In some embodiments, the first portion of photons and the second portion of photons may be collimated by a first set of first pinholes and a second set of second pinholes of a collimator of a SPECT device. Each second pinhole of the second set of second pinholes may be equipped with a filter.

In some embodiments, the first energy and the second energy may correspond to two characteristic peaks of a radioactive tracer, respectively.

In some embodiments, to generate an image based on the first projection data set and the second projection data set, the system may determine a first piece of data corresponding to the first set of first pinholes and a second piece of data corresponding to the second set of second pinholes based on the first projection data set, the second projection data set, and a first matrix associated with the filters. The first piece of data may be associated with a first count of photons, among the first portion of photons and the second portion of photons, that pass through the first set of first pinholes. The second piece of data may be associated with a second count of photons, among the first portion of photons and the second portion of photons, that pass through the second set of second pinholes. The system may further reconstruct the image based on the first piece of data and the second piece of data.

In some embodiments, the first matrix may be further associated with yield abundances of the radioactive tracer at the first energy and the second energy.

In some embodiments, to generate an image based on the first projection data set and the second projection data set, the system may determine a second matrix. The second matrix may include a first sub-matrix associated with the first set of first pinholes, and a second sub-matrix associated with the second set of second pinholes. The system may further reconstruct the image based on the first projection data set, the second projection data set, the second matrix, and a first matrix associated with the filters.

In some embodiments, to determine a second matrix, the system may determine the first sub-matrix associated with the first set of first pinholes and determine the second sub-matrix associated with the second set of second pinholes.

In some embodiments, to determine the first sub-matrix associated with the first set of first pinholes, the system may obtain a first simulation image generated when the second set of second pinholes are covered using a cover plate. The cover plate may be configured to prohibit photons from passing through the second pinholes. The first simulation image may include a plurality of pixels. The system may further determine simulation projection data corresponding to each of the plurality of pixels and determine the first sub-matrix based on the simulation projection data.

In some embodiments, to determine the first sub-matrix associated with the first set of first pinholes, the system may determine a plurality of point spread functions (PSFs) of points at different positions in a field of view (FOV) of the SPECT device. When the second set of second pinholes are covered using a cover plate, the cover plate may be configured to prohibit photons from passing through the second pinholes. The system may further determine the first sub-matrix based on the plurality of PSFs.

In some embodiments, to determine the second sub-matrix associated with the second set of second pinholes, the system may obtain a second simulation image generated when the first set of first pinholes are covered using a cover plate. The cover plate may be configured to prohibit photons from passing through the first pinholes. The second simulation image may include a plurality of pixels. The system may further determine simulation projection data corresponding to each of the plurality of pixels and determine the second sub-matrix based on the simulated projection data.

In some embodiments, to determine the second sub-matrix associated with the second set of second pinholes, the system may determine a plurality of point spread functions (PSFs) of points at different positions in a field of view (FOV) of the SPECT device. When the first set of first pinholes are covered using a cover plate, the cover plate may be configured to prohibit photons from passing through the first pinholes. The system may further determine the second sub-matrix based on the plurality of PSFs.

In some embodiments, to generate an image, the system may generate the image using a maximum likelihood expectation maximization (MLEM) algorithm.

In some embodiments, the first set of first pinholes may be patterned such that first projections of a field of view (FOV) of the SPECT device through the first set of first pinholes onto a detector of the SPECT device have no overlapping region. The second set of second pinholes may be patterned such that second projections of the FOV of the SPECT device through the second set of second pinholes onto the detector have no overlapping region. At least one of the first projections may be overlapped with at least one of the second projections.

In some embodiments, the radioactive tracer may include at least one of indium-111, or iodine-131.

According to yet another aspect of the present disclosure, a method for single-photon emission computed tomography (SPECT) imaging is provided. The method may be implemented on at least one computing device, each of which may include at least one processor and a storage device. The method may include obtaining a first projection data set associated with a first portion of photons each of which having a first energy and a second projection data set associated with a second portion of photons each of which having a second energy. The method may further include generating an image based on the first projection data set and the second projection data set.

According to yet another aspect of the present disclosure, a non-transitory computer-readable medium storing at least one set of instructions for single-photon emission computed tomography (SPECT) imaging is provided. When executed by at least one processor, the at least one set of instructions may direct the at least one processor to perform a method. The method may include obtaining a first projection data set associated with a first portion of photons each of which having a first energy and a second projection data set associated with a second portion of photons each of which having a second energy. The method may further include generating an image based on the first projection data set and the second projection data set.

According to yet another aspect of the present disclosure, a collimator for single-photon emission computed tomography (SPECT) imaging is provided. The collimator may include a first set of first pinholes and a second set of second pinholes. Each second pinhole of the second set of second pinholes may be equipped with a filter configured to filter photons.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not scaled. These embodiments are non-limiting exemplary embodiments, in which like reference numerals represent similar structures throughout the several views of the drawings, and wherein:

FIG. 8 is a schematic flowchart illustrating an exemplary process for generating an image according to some embodiments of the present disclosure;

FIG. 9A illustrates a cross-sectional view of a phantom according to some embodiments of the present disclosure;

FIG. 9B illustrates an image of the phantom in FIG. 9A according to some embodiments of the present disclosure;

FIG. 9C illustrates an image of the phantom in FIG. 9A according to some embodiments of the present disclosure;

FIG. 9D illustrates an image of the phantom in FIG. 9A according to some embodiments of the present disclosure;

FIG. 9E illustrates an image of the phantom in FIG. 9A according to some embodiments of the present disclosure.

DETAILED DESCRIPTION

Figure 1:
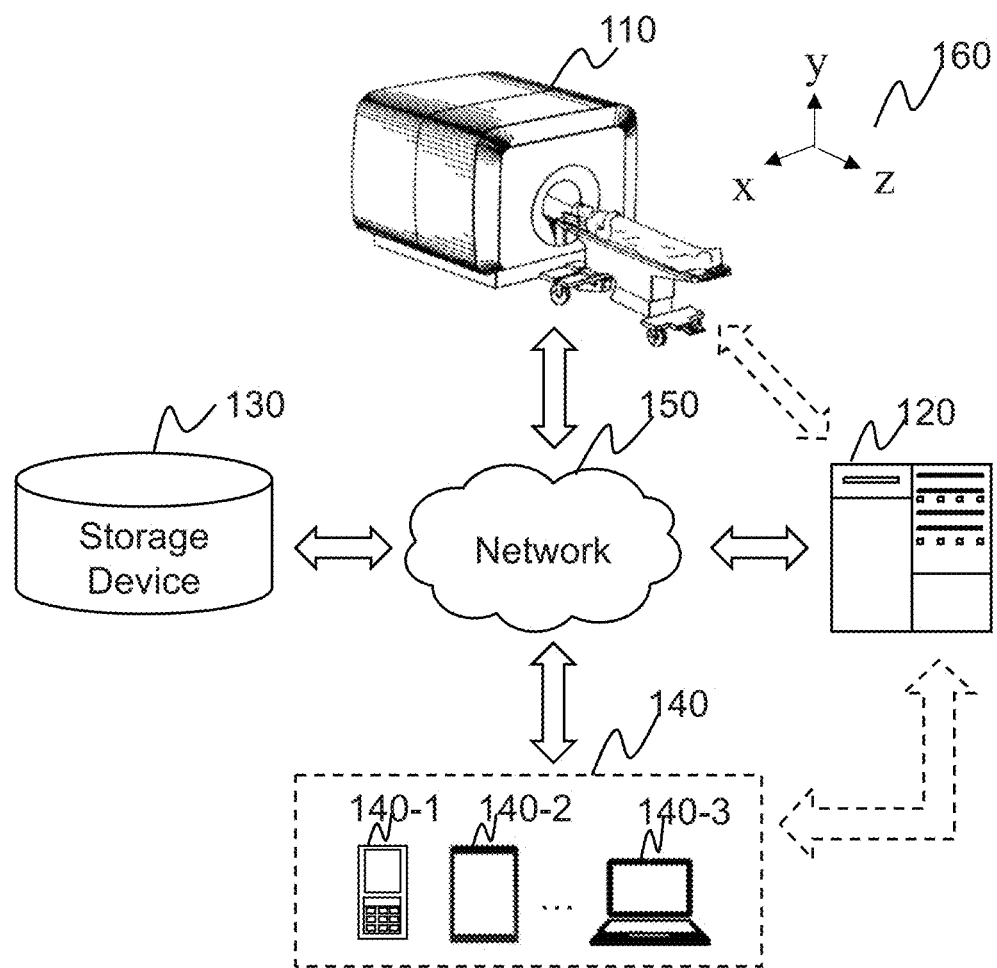
FIG. 1 is a schematic diagram illustrating an exemplary imaging system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

According to one aspect of the present disclosure, an imaging system may be provided. The imaging system may include a detector and a collimator. The detector may be configured to detect photons. The collimator may have at least two sets of pinholes. The at least two sets of pinholes may include a first set of first pinholes and a second set of second pinholes. Each second pinhole of the second set of second pinholes may be equipped with a filter configured to filter the photons. According to another aspect of the present disclosure, a method for generating an image may be provided. A first projection data set associated with a first portion of photons each of which having a first energy may be obtained. A second projection data set associated with a second portion of photons each of which having a second energy may be obtained. An image may be generated based on the first projection data set and the second projection data set.

In some embodiments, the first projection data set and the second projection data set may be obtained using the imaging system provided in the present disclosure. Accordingly, compared to using an imaging system with a traditional collimator that only has pinholes without filters, by using the collimator that has the first set of first pinholes without filters and the second set of pinholes with filters, more photons may be allowed to pass through the collimator and be detected, thereby improving the sensitivity of the imaging system. The two sets of pinholes may be configured to perform spectral filtrations on the photons. Besides, by using the collimator that has two sets of pinholes and using a radioactive tracer having at least two characteristic peaks, the detector may acquire multiplexing projection data with different spectral sensitivity, and the multiplexing projection data may be encoded with spectral filtrations and be decomposed, and thus, a higher contrast to noise ratio of the imaging system may be achieved, and the sensitivity may be further improved. Because the second pinholes are equipped with filters that can filter photons of different energies at different ratios, an image without multiplexing artifacts may be generated based on the projection data (i.e., the first projection data set and second projection data set) obtained by the imaging system, thereby improving the sensitivity and the accuracy of the imaging system. Moreover, due to the use of the two sets of pinholes, the angular sampling of the imaging system may be improved, which may be beneficial to improve spatial resolution and reduce aliasing artifacts of the imaging system.

FIG. 1 is a schematic diagram illustrating an exemplary imaging system according to some embodiments of the present disclosure. In some embodiments, the imaging system 100 may be a single-modality system or a multi-modality system. Exemplary single-modality systems may include a single-photon emission computed tomography (SPECT) system, a positron emission tomography (PET) system, etc. Exemplary multi-modality systems may include a SPECT-CT system, a SPECT-PET system, a SPECT-magnetic resonance (SPECT-MR) system, etc. In some embodiments, the imaging system 100 may include modules and/or components for performing imaging and/or related analysis.

Merely by way of example, as illustrated in FIG. 1, the imaging system 100 may include an imaging device 110, a processing device 120, a storage device 130, one or more terminal devices 140, and a network 150. The components in the imaging system 100 may be connected in one or more of various ways. Merely by way of example, the imaging device 110 may be connected to the processing device 120 through the network 150. As another example, the imaging device 110 may be connected to the processing device 120 directly as illustrated in FIG. 1. As a further example, the terminal device 140 may be connected to another component of the imaging system 100 (e.g., the processing device 120) via the network 150. As still a further example, the terminal device 140 may be connected to the processing device 120 directly as illustrated by the dotted arrow in FIG. 1. As still a further example, the storage device 130 may be connected to another component of the imaging system 100 (e.g., the processing device 120) directly as illustrated in FIG. 1, or through the network 150.

The imaging device 110 may be configured to acquire imaging data relating to at least one part of an object. For example, the imaging device 110 may scan an object or a portion thereof that is located within its detection region and generate projection data relating to the object or the portion thereof. The imaging data relating to at least one part of an object may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. The object may be biological or non-biological. For example, the object may include a patient, an animal, a man-made object (e.g., a phantom), etc. As another example, the object may include a specific portion, organ, and/or tissue of the patient. For example, the object may include the head, the neck, the thorax, the heart, the stomach, a blood vessel, soft tissue, a tumor, nodules, or the like, or any combination thereof. In some embodiments, the imaging device 110 may include a single modality imaging device. For example, the imaging device 110 may include a single-photon emission computed tomography (SPECT) device, a positron emission tomography (PET) device, etc. In some embodiments, the imaging device 110 may include a multi-modality imaging device. Exemplary multi-modality imaging devices may include a SPECT-CT device, a SPECT-PET device, a SPECT-MR device, etc.

A SPECT device may be taken as an example of the imaging device 110, and not intended to limit the scope of the present disclosure. The SPECT device may include a gantry, a collimator, a detector, an electronics module, and/or other components not shown. The gantry may support one or more parts of the SPECT device, for example, the collimator, the detector, the electronics module, and/or other components. The collimator may collimate photons (e.g., y photons) emitted from an object being examined. In some embodiments, the collimator may be a multi-pinhole collimator having at least two sets of pinholes. The at least two sets of pinholes may include a first set of first pinholes and a second set of second pinholes. In some embodiments, one or more second pinholes (e.g., each second pinhole) of the second set of second pinholes may be equipped with a filter configured to filter the photons. The detector may be configured to detect the photons collimated by the collimator and/or generate electrical signals. The electronics module may collect and/or process electrical signals (e.g., scintillation pulses) generated by the detector. The electronics module may convert an analog signal (e.g., an electrical signal generated by the detector) relating to a photon detected by the detector to a digital signal to generate projection data. In some embodiments, the electronics module may be part of the detector. More descriptions regarding the imaging device may be found elsewhere of the present disclosure (e.g., FIG. 4 and the descriptions thereof).

The processing device 120 may process data and/or information obtained from the imaging device 110, the terminal device 140, and/or the storage device 130. For example, the processing device 120 may obtain projection data acquired by the imaging device 110. The processing device 120 may generate an image based on the projection data. As another example, the processing device 120 may determine a system matrix of the imaging device 110. The processing device 120 may generate the image further based on the system matrix. In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the imaging device 110, the terminal device 140, and/or the storage device 130 via the network 150. As another example, the processing device 120 may be directly connected to the imaging device 110, the terminal device 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal device 140 and/or the processing device 120. The data may include imaging data acquired by the processing device 120, algorithms and/or models for processing the imaging data, etc. For example, the storage device 130 may store imaging data (e.g., SPECT images, SPECT projection data, etc.) acquired by the imaging device 110. As another example, the storage device 130 may store one or more algorithms (e.g., a maximum likelihood expectation maximization (MLEM) algorithm) for processing the imaging data, etc. In some embodiments, the storage device 130 may store data and/or instructions that the processing device 120 may execute or use to perform exemplary methods/systems described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal device 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal device 140, etc.). In some embodiments, the storage device 130 may be part of the processing device 120.

The terminal device 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 140 may be part of the processing device 120.

The network 150 may include any suitable network that can facilitate the exchange of information and/or data for the imaging system 100. In some embodiments, one or more components of the imaging device 110 (e.g., a SPECT device, a SPECT-CT device, etc.), the terminal device 140, the processing device 120, the storage device 130, etc., may communicate information and/or data with one or more other components of the imaging system 100 via the network 150. For example, the processing device 120 may obtain data from the imaging device 110 via the network 150. As another example, the processing device 120 may obtain user instructions from the terminal device 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

In some embodiments, a three-dimensional coordinate system 160 may be used in the imaging system 100 as illustrated in FIG. 1. A first axis may be parallel to the lateral direction of a table (e.g., the x-axis direction as shown in FIG. 1). A second axis may be parallel to the longitudinal direction of the table (e.g., the z-direction as shown in FIG. 1). A third axis may be parallel to a vertical direction of the table (e.g., the y-axis direction as shown in FIG. 1). The origin of the three-dimensional coordinate system 160 may be any point in the space. In some embodiments, the origin of the three-dimensional coordinate system 160 may be determined by an operator. In some embodiments, the origin of the three-dimensional coordinate system 160 may be determined by the imaging system 100.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios.

Figure 2:
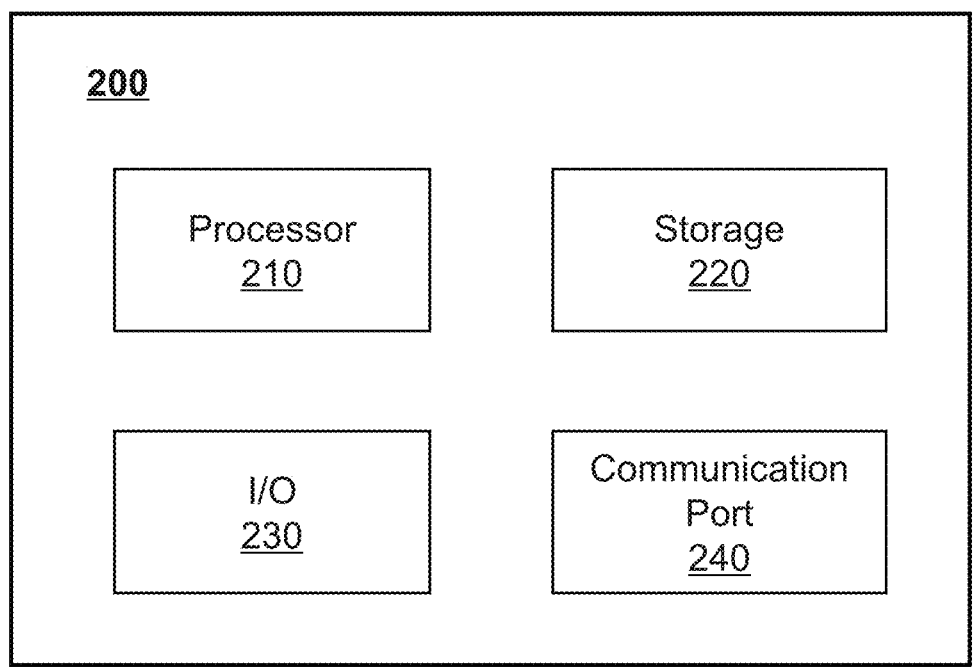
FIG. 2 is a schematic diagram illustrating hardware and/or software components of an exemplary computing device according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the imaging device 110, the terminal device 140, the storage device 130, and/or any other component of the imaging system 100. Specifically, the processor 210 may process one or more measured data sets obtained from the imaging device 110. For example, the processor 210 may generate an image based on the data set(s). In some embodiments, the generated image may be stored in the storage device 130, the storage 220, etc. In some embodiments, the generated image may be displayed on a display device by the I/O 230. In some embodiments, the processor 210 may perform instructions obtained from the terminal device 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal device 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for generating a SPECT image based on a first projection data set associated with a first portion of photons each of which having a first energy, and a second projection data set associated with a second portion of photons each of which having a second energy.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the imaging device 110, the terminal device 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
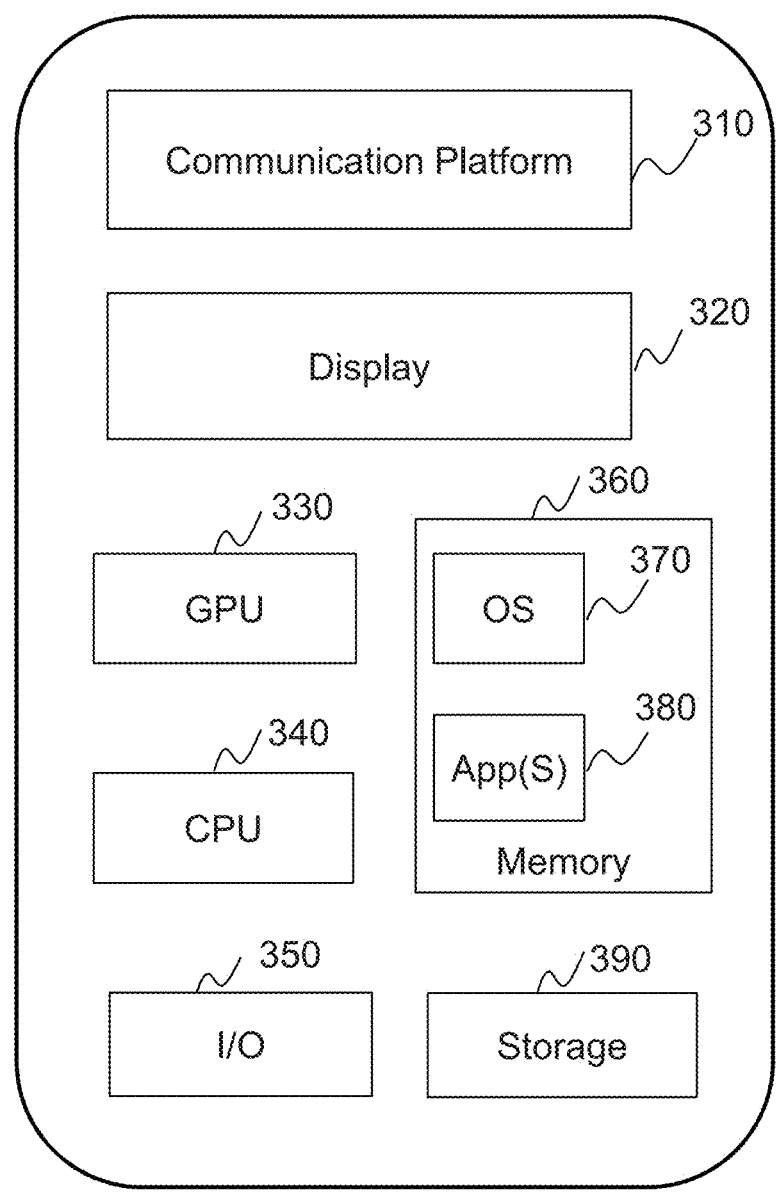
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 150.

To implement various modules, units, and functionalities described in the present disclosure, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
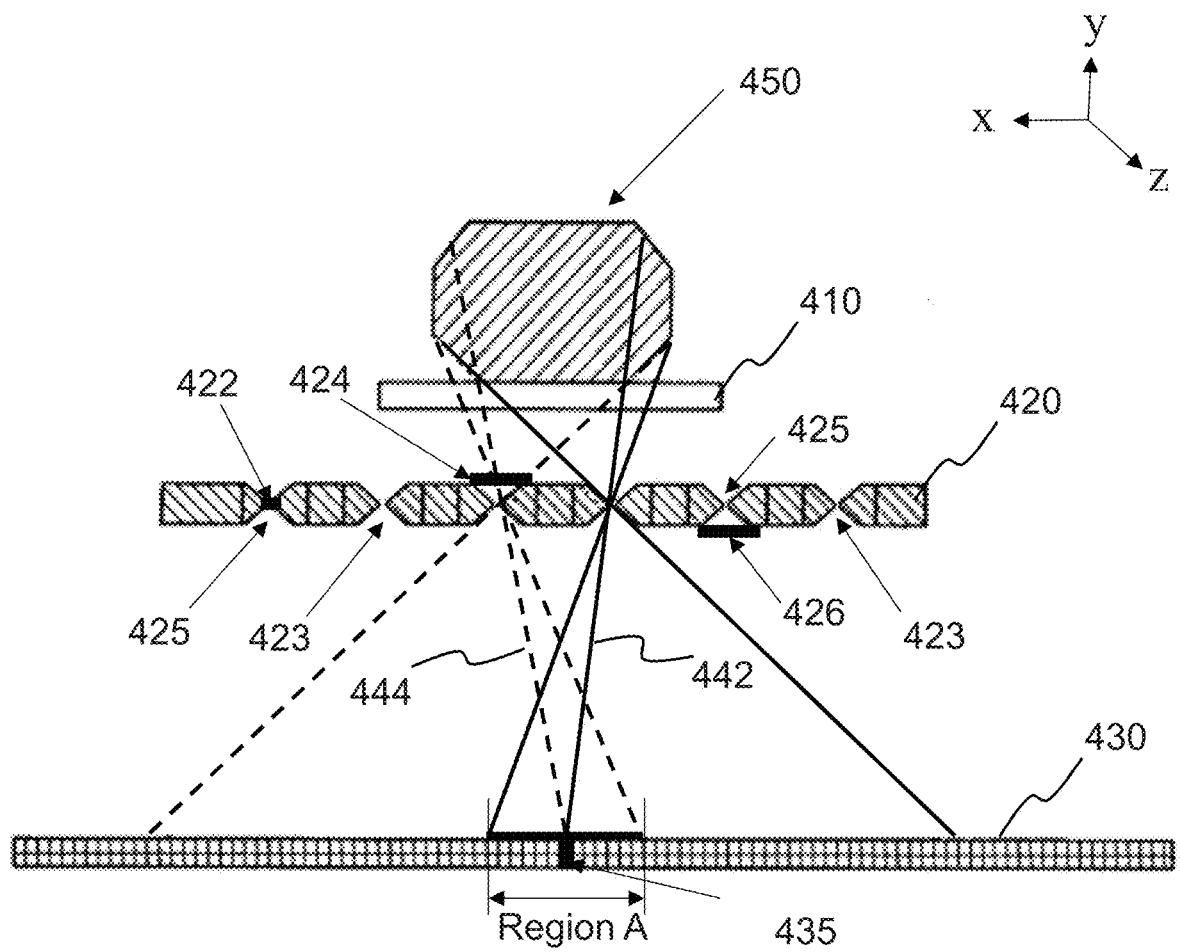
FIG. 4 is a schematic diagram illustrating a cross-sectional view of a portion of an exemplary imaging device according to some embodiments of the present disclosure.

FIG. 4 is a schematic diagram illustrating a cross-sectional view of a portion of an exemplary imaging device according to some embodiments of the present disclosure. In some embodiments, an imaging device 400 illustrated in FIG. 4 may be part of the imaging device 110. As shown in FIG. 4, the imaging device 400 may include a table 410, a collimator 420, and a detector 430.

The table 410 may be configured to support an object to be examined. In some embodiments, the object may include the neck, the heart, the abdomen, a lung, or the like, or any combination thereof. In some embodiments, the object may be injected with a radioactive tracer before being scanned by the imaging device 400. For example, the object may be scanned by the imaging device 400 in a predetermined time period after the radioactive tracer is injected into the object. As another example, the object may be scanned by the imaging device 400 in a certain time period after the tracer distribution in the object reaches equilibrium or steady-state. In some embodiments, the radioactive tracer may include technetium-99 (Tc-99), fluorine-18 (F-18), indium-111 (In-111), iodine-131 (I-131), or the like, or any combination thereof.

An energy spectrum of the radioactive tracer may have one or more characteristic peaks each of which corresponds to an energy. For brevity, the one or more characteristic peaks of the energy spectrum of the radioactive tracer may also be referred to as the one or more characteristic peaks of the radioactive tracer. As used herein, a characteristic peak corresponding to an energy refers to the main energy emission from the decay of the radioactive tracer injected in the object. In some embodiments, an energy range (also referred to as an energy window of the detector 430) of the photons detected by the detector 430 may be associated with the energies corresponding to the characteristic peak(s) of the radioactive tracer. Specifically, the energy window may include energies within an energy threshold range around the energy of a characteristic peak. For example, if an energy corresponding to a characteristic peak is 150 keV, and the energy threshold range is 25 keV, then the energy window may be determined as [125 keV, 175 keV]. In some embodiments, the energy window may be determined based on one or more energy values. In some embodiments, the energy value may be set according to a default setting of the imaging device 400 or preset by a user or operator via the terminal device 140.

It should be noted that if a measured energy of a photon falls within an energy window corresponding to a specific energy, it may mean that the energy of the photon is considered as the specific energy, i.e., the photon has the specific energy. In some embodiments, the photons emitted from the object (e.g., the object injected with the radioactive tracer having one or more characteristic peaks) may be measured as having one or more energies corresponding to the characteristic peak(s). For example, for technetium-99 (Tc-99) having a characteristic peak at 141 keV, photons emitted by Tc-99 (or the object injected with Tc-99) may have an energy of 141 keV. In some embodiments, if the measured energy of a photon is close to a specific energy (e.g., a difference between the measured energy and the specific energy is less than a threshold), the photon may be considered as having the specific energy. For instance, a photon with a measured energy of 137 keV may be regarded as a photon with an energy of 141 keV (or the photon with a measured energy of 137 keV may be regarded as having an energy of 141 keV). As another example, for indium-111 (In-111) having two characteristic peaks at 171 keV and 245 keV, respectively, two energy windows corresponding to the energy of 171 keV and the energy of 245 keV may be determined by an energy value (e.g., 208 keV). For instance, a first energy window corresponding to the energy of 171 keV may include energies less than the energy value (e.g., 208 keV), and a second energy window corresponding to the energy of 245 keV may include energies that exceeds the energy value (e.g., 208 keV). It should be noted that the energy value of 208 keV may be either assigned to the first energy window or the second energy window. In this case, if a measured energy of a photon is 190 keV, the photon may be regarded as a photon with an energy of 171 keV (or the photon with a measured energy of 190 keV may be regarded as having an energy of 171 keV). If a measured energy of a photon is 210 keV, the photon may be regarded as a photon with an energy of 245 keV (or the photon with a measured energy of 210 keV may be regarded as having an energy of 245 keV).

In some embodiments, the characteristic peak(s) of the radioactive tracer may be designated or inputted by a user via the terminal device 140. For example, for a radioactive tracer whose energy spectrum has no characteristic peak, the user may designate characteristic peak(s) corresponding to one or more energies of the radioactive tracer. In some embodiments, two or more radioactive tracers each of which has only one characteristic peak (also referred to as a single-energy isotope tracer or a single-peak isotope tracer) may be injected into the object at a certain ratio. For example, two single-energy isotope tracers having different characteristic peaks may be injected into the object at a certain ratio. The two single-energy isotope tracers at the certain ratio may be equivalent to a radioactive tracer having two characteristic peaks (also referred to as a dual-energy isotope tracer or a dual-peak isotope tracer).

The collimator 420 may be configured to collimate the photons emitted from the object. In some embodiments, the collimator 420 may be a multi-pinhole collimator having at least two sets of pinholes. Each set of pinholes may include one or more pinholes. For example, as shown in FIG. 4, the collimator 420 may have a first set of first pinholes 423 and a second set of second pinholes 425. In some embodiments, one or more second pinholes (e.g., each second pinhole) of the second set of second pinholes 425 may be equipped with filters (e.g., a filter 422, 424, or 426). The filters may be configured to filter the photons. In other words, the filters may prevent a portion of the photons from passing through the second pinholes and allow the remaining portion of the photons to pass through the second pinholes. As a result, a count or number of photons filtered by the filters may change. In some embodiments, one or more first pinholes (e.g., each first pinhole) of the first set of first pinholes 423 may be equipped with first filters, and one or more second pinholes (e.g., each second pinhole) of the second set of second pinholes 425 may be equipped with second filters different from the first filters. For example, the second filters and the first filters may have different thicknesses. As another example, the material of the second filters may be different from the material of the first filters. In some embodiments, the collimator 420 may be made of a heavy metal such as lead, tungsten, gold, etc. The thickness of the collimator 420 may relate to the energy of photons that the imaging system 100 is desired to detect. For example, the thickness of the collimator 420 may be large enough to prevent the majority of the photons from penetrating the collimator 420, so that photons primarily pass through the pinholes on the collimator 420.

In some embodiments, each pinhole (i.e., the first pinhole or the second pinhole) of the collimator 420 may have a size (or diameter), a shape, etc. In some embodiments, the sizes of the pinholes of the collimator 420 may be the same or different. For example, if a pinhole is relatively close to the object or a field of view (FOV) 450 of the imaging device 400, the size of the pinhole may be relatively small. In some embodiments, the shapes of the pinholes of the collimator 420 may be the same or different. For example, the shapes of the pinholes may include a funnel shape, a "V" shape, a double conical shape, or the like, or any combination thereof.

Figure 5A:
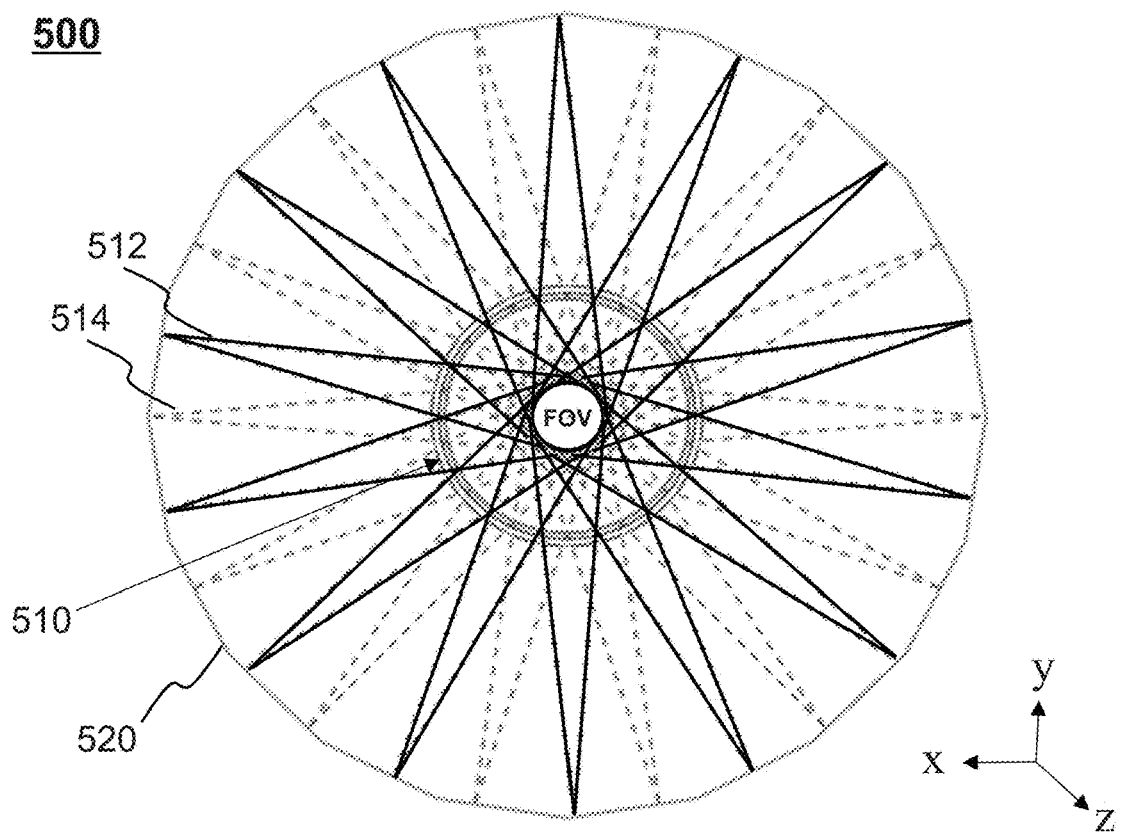
FIG. 5A is a schematic diagram illustrating a cross-sectional view of a portion of an exemplary imaging device along a transaxial direction according to some embodiments of the present disclosure.
Figure 5B:
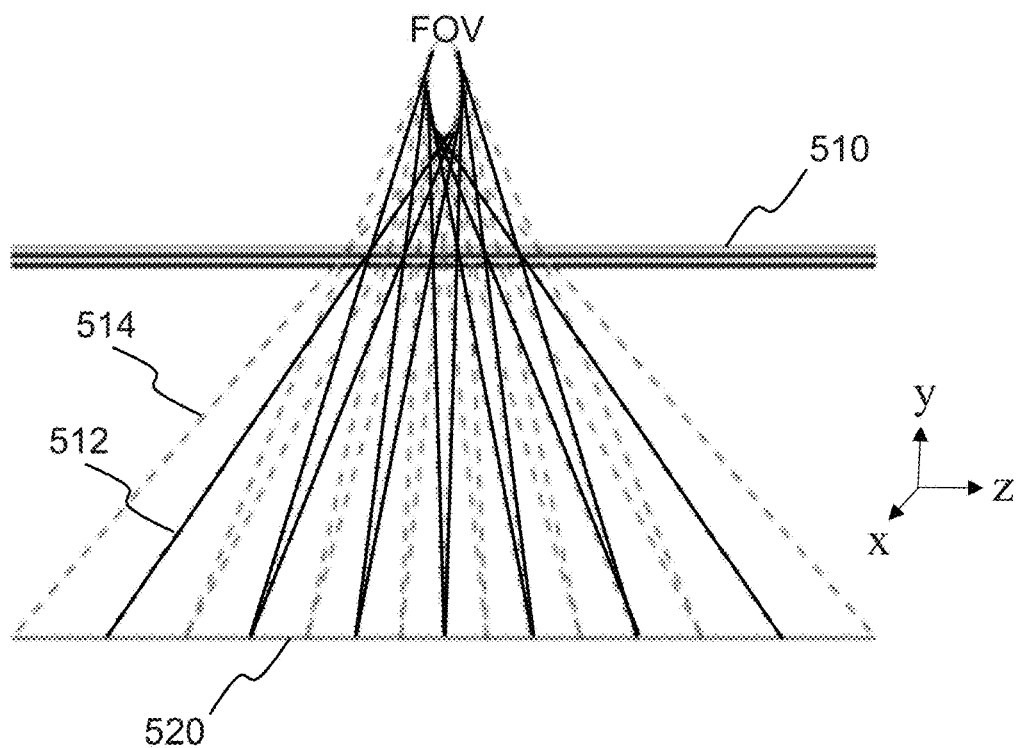
FIG. 5B is a schematic diagram illustrating a cross-sectional view of an imaging device in FIG. 5A along an axial direction according to some embodiments of the present disclosure.

In some embodiments, each set of pinholes may include two or more pinholes. The first set of first pinholes 423 may be patterned such that first projections (e.g., as indicated by the solid lines 512 in FIGS. 5A and 5B) of the FOV 450 of the imaging device 400 through the first set of first pinholes 423 onto the detector 430 have no overlapping region. As used herein, a projection of the FOV of the imaging device through a pinhole onto the detector corresponds to a region where the photons emitted from the object in the FOV fall on the detector after passing through the pinhole. Thus, the first projections having no overlapping region may refer that photons passing through different first pinholes may fall in different regions on the detector. The second set of second pinholes 425 may be patterned such that second projections (e.g., as indicated by the dashed lines 514 in FIGS. 5A and 5B) of the FOV 450 of the imaging device 400 through the second set of second pinholes 425 onto the detector 430 have no overlapping region. Similarly, the second projections having no overlapping region may refer that photons passing through different second pinholes may fall in different regions on the detector. In some embodiments, the first projections and/or the second projections may cover the entire detector 430. In some embodiments, at least one of the first projections may be overlapped with at least one of the second projections. In other words, a detector unit corresponding to an overlapping region between the at least one of the first projections and the at least one of the second projections may detect both photons passing through a first pinhole corresponding to the at least one of the first projections and photons passing through a second pinhole corresponding to the at least one of the second projections. In some embodiments, because at least one of the first projections is overlapped with at least one of the second projections, the collimator having the at least two sets of pinholes may also be referred to as a spectral multiplexing collimator in the present disclosure. As illustrated in FIG. 4, solid lines represent first auxiliary lines of first projections of the FOV 450 of the imaging device 400 through the first pinhole(s) 423 onto the detector 430, and dashed lines represent second auxiliary lines of second projections of the FOV 450 through the second set of second pinholes 425 onto the detector 430. An auxiliary line may correspond to a projection line of the FOV (or object). As used herein, a projection line refers to a line from a site (in the FOV) of a photon emitted from the object to a site where the photon falls on the detector. Region A in FIG. 4 illustrates an exemplary overlapping region between the first projections and the second projections. In some embodiments, at least one of the first projections may be overlapped with at least two of the second projections (e.g., as shown in FIGS. 5A and 5B).

Figure 6:
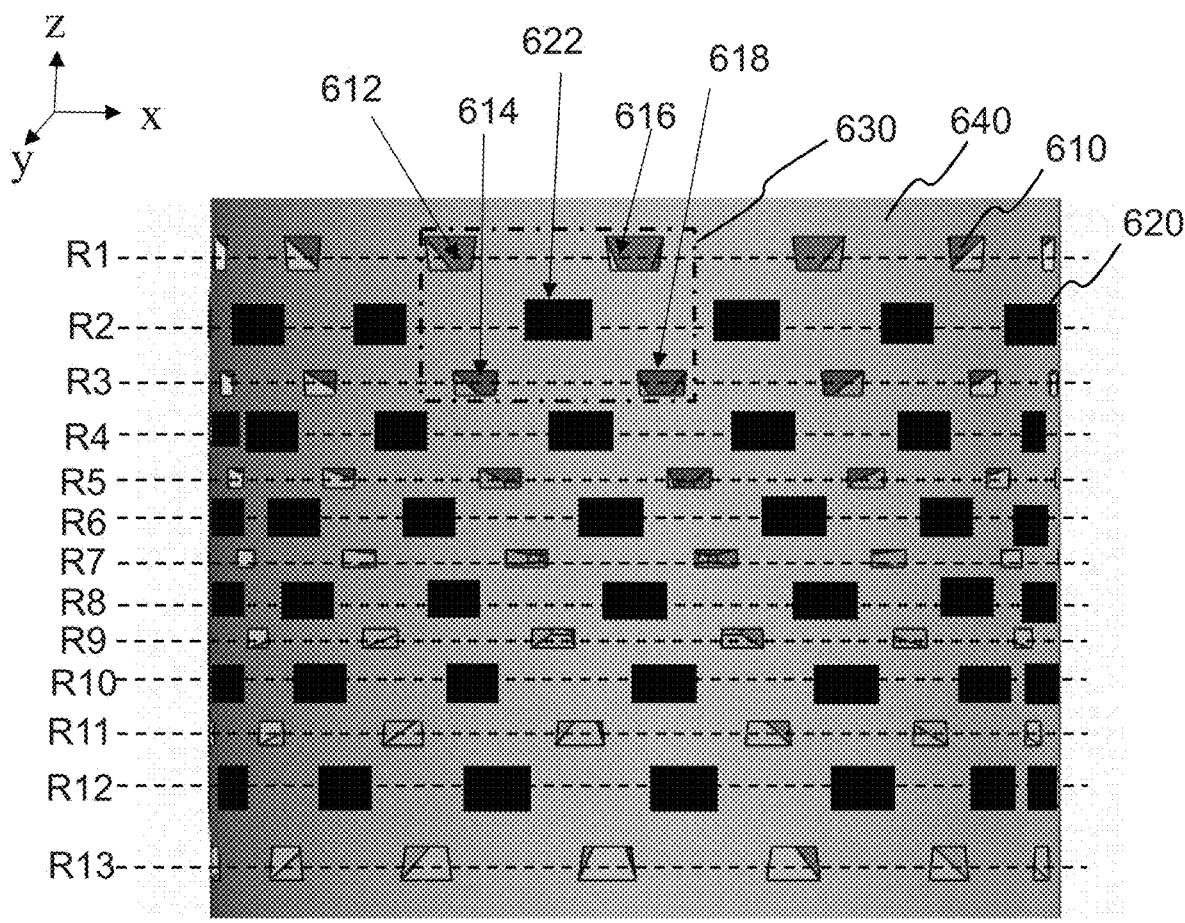
FIG. 6 is a schematic diagram illustrating an exemplary arrangement of pinholes of a ring shaped collimator according to some embodiments of the present disclosure.

In some embodiments, the second set of second pinholes may interleave between the first set of first pinholes. In other words, the second pinholes may be arranged in one or more areas between the first pinholes. For example, the first set of first pinholes and the second set of second pinholes may be arranged in a manner similar to that illustrated in FIG. 6. In some embodiments, the first set of first pinholes may include a first count of rows of first pinholes, and the second set of second pinholes may include a second count of rows of second pinholes (e.g., as shown in FIG. 6). One or more rows (e.g., each row) of pinholes may be arranged in any direction, such as a transaxial direction (e.g., the x-axis direction in FIG. 1) or an axial direction (e.g., the z-axis direction in FIG. 1) of the imaging device 400. In some embodiments, one or more rows (e.g., each row) of first pinholes may be equally spaced. In some embodiments, one or more rows (e.g., each row) of second pinholes may be equally spaced. In some embodiments, spacings between a row of first pinholes may be equal to spacings between a row of second pinholes. In some embodiments, at least one second pinhole of the second set of pinholes may be arranged at a center of a region encompassing four first pinholes adjacent to the at least one second pinhole. Alternatively or additionally, in some embodiments, at least one first pinhole of the first set of pinholes may be arranged at a center of a region encompassing four second pinholes adjacent to the at least one first pinhole. In some embodiments, the second count may be greater than, equal to, or less than the first count. For example, the first set of first pinholes may include 7 rows of first pinholes in the axial direction, and the second set of second pinholes may include 6 rows of second pinholes in the axial direction.

In some embodiments, the collimator 420 may be plate shaped or ring shaped. The detector 430 may also be plate shaped or ring shaped. For example, as shown in FIG. 4, the collimator 420 may be configured as a collimator plate, and the detector 430 may also be configured as a detector plate, which is not intended to limit the scope of the present disclosure. As another example, the collimator 420 may be configured as a collimator plate, and the detector 430 may be ring shaped (e.g. a cylinder). As still an example, the collimator 420 may be ring shaped, and the detector 430 may be configured as a detector plate. As still a further example, the collimator 420 may be ring shaped, and the detector 430 may be ring shaped accordingly. The detector 430 may be concentric with the collimator 420. More descriptions about the ring shaped collimator and/or ring shaped detector may be found elsewhere in the present disclosure (e.g., FIG. 5A, FIG. 5B and FIG. 6 and the descriptions thereof). In some embodiments, if the collimator 420 and/or the detector 430 are plate shaped, the collimator 420 and/or the detector 430 may be set on a rotatable gantry to rotate around the object when the object is scanned by the imaging device 400. In some embodiments, the imaging device 400 may include two or more collimator plates to achieve photon detection from multiple sampling angles.

The filter may filter photons with different energies at different ratios. Specifically, the filter may filter photons with different energies at different ratios of a count or number of photons. In some embodiments, after being filtered by the filter, a ratio of a count or number of photons with a first energy to a count or number of photons with a second energy may be changed. Because a second pinhole is equipped with a filter, the ratio of photons with different energies may be changed after the photons pass through the second pinhole. If a first pinhole is equipped without a filter, the ratio of photons with different energies may not be changed after the photons pass through the first pinhole. Therefore, a first ratio of photons with different energies passing through the first set of first pinholes and a second ratio of photons with different energies passing through the second set of second pinholes may be different. For example, the filter may filter (or shield) 20% of a total count of photons of a first energy (e.g., a relatively high energy), and the filter may filter 40% of a total count of photons of a second energy (e.g., a relatively low energy). According to the above-mentioned example, for a beam of photons in which the ratio of a count (or number) of photons with different energies is 1:1, a first ratio of the count of photons (among the beam of photons) with the first energy to the count of photons (among the beam of photons) with the second energy may be substantially 1:1, after the beam of photons pass through the first set of first pinholes 423. A second ratio of the count of photons (among the beam of photons) with the first energy to the count of photons (among the beam of photons) with the second energy may be 8:6, after the beam of photons pass the second set of second pinholes 425. It should be noted that if a first pinhole is equipped with a first filter and a second pinhole is equipped with a second filter different from the first filter, a change of the ratio of photons with different energies after the photons pass through the first pinhole may be different from a change of the ratio of photons with different energies after the photons pass through the second pinhole. As a result, a first ratio of photons with different energies passing through the first set of first pinholes and a second ratio of photons with different energies passing through the second set of second pinholes may be different.

According to the present disclosure, if the at least one of the first projections is overlapped with the at least one of the second projections (i.e., multiplexing projections are formed), the multiplexing projections may be encoded by equipping the second set of second pinholes with filters (or equipping the first set of first pinholes and the second set of second pinholes with different filters). That is, using the filters, the multiplexing projections on the detector may be formed by different ratios of photons with different energies, which may allow for the decomposition of the multiplexing projections. Specifically, for a multiplexing projection (e.g., a projection on the detector unit 435 in region A in FIG. 4), the detector unit 435 may detect a cumulative count of photons with the first energy and a cumulative count of photons with the second energy. A first total count of photons passing through the first pinhole and a second total count of photons passing through the second pinhole may be determined based on the cumulative count of photons with the first energy, the cumulative count of photons with the second energy, and the ratio difference between the first ratio and the second ratio. Further, an image may be generated based on a plurality of first total counts (also referred to as a first piece of data) and a plurality of second total counts (also referred to as a second piece of data). More descriptions for generating an image based on the first piece of data and the second piece of data may be found elsewhere of the present disclosure (e.g., FIG. 8 and the descriptions thereof).

In some embodiments, the filter may be made of a heavy metal. For example, the filter may include a heavy metal sheet of a certain thickness. In some embodiments, the heavy metal sheet may include a tungsten sheet, a gold sheet, a copper sheet, a lead sheet, or the like, or any combination thereof. In some embodiments, the filter may have a thickness in a range from 0.01 mm to 1 mm, such as 0.1 mm, 0.2 mm, 0.35 mm, 0.5 mm, etc. It should be noted that filters with different thicknesses and/or materials may have different filter transmissivities for different energies, which may affect the imaging effect of the imaging device 400. In some embodiments, the material and/or the thickness of the filter may be selected based on the characteristics of the radioactive tracer, system geometry parameters of the imaging device 400, a target (or desired) sensitivity of the imaging device, or the like, or a combination thereof. Exemplary system geometry parameters may include parameters associated with a size of the collimator (e.g., a radius of a transaxial section of a cylindrical collimator, an area of a collimator plate), a size of the detector, sizes and positions of the pinholes on the collimator, a size of the FOV, a resolution of the detector, or the like, or any combination thereof.

Specifically, the thickness of the filter may be negatively correlated with the sensitivity of the imaging device and positively correlated with the spatial resolution of the imaging device. Thus, the thickness design of the filter may need to weigh the sensitivity of the imaging device and the spatial resolution of the imaging device. More descriptions regarding the trade-off between the sensitivity of the imaging device and the spatial resolution of the imaging device may be found elsewhere in the present disclosure (e.g., FIG. 8 and the descriptions thereof).

In some embodiments, the filter may be disposed at any position of each second pinhole, as long as the photons can be filtered when passing through the second hole. For example, the filter (e.g., the filter 422) may be disposed in a central region of the second pinhole. As another example, the filter (e.g., the filter 424) may be disposed on a surface of the collimator 420 facing the table 410, that is, the filter may cover the second pinhole. As a further example, the filter (e.g., the filter 426) may be disposed on a surface of the collimator 420 facing the detector 430.

In some embodiments, the shape of the filter may match the corresponding pinhole. In some embodiments, an area of the filter may be greater than a size of the corresponding pinhole(s). In some embodiments, the filter may be embedded in a second pinhole (e.g., the filter 422), cover a surface of the collimator close to the table corresponding to a second pinhole (e.g., the filter 424), cover a surface of the collimator close to the detector corresponding to a second pinhole (e.g., the filter 426), or be disposed by a distance (e.g., 0.5 mm, 1 mm, etc.) above a second pinhole. In some embodiments, one or more filters and the collimator may be configured as one piece. In some embodiments, two or more filters may be configured as a filter plate. In such cases, the filter plate may include one or more holes corresponding to one or more first pinholes.

The detector 430 may be configured to detect the photons collimated by the collimator 420. The detector 430 may be used for multiplex detection of the photons with different energies each of which corresponds to one characteristic peak of the radioactive tracer. For example, the detector 430 may detect a cumulative count of photons with the first energy and a cumulative count of photons with the second energy. That is, the detector 430 may perform the detection of multiplexing channels of signals (e.g., the cumulative count of photons with the first energy and the cumulative count of photons with the second energy). A portion of the photons with the first energy may pass through the first set of first pinholes and be detected by the detector, and another portion of the photons with the first energy may pass through the second set of second pinholes and be detected by the detector. Similarly, a portion of the photons with the second energy may pass through the first set of first pinholes and be detected by the detector, and another portion of the photons with the second energy may pass through the second set of second pinholes and be detected by the detector. In some embodiments, the detector 430 may include a plurality of detector units each of which includes multiple channels. In some embodiments, if first projections and second projections have an overlapping region on the detector, each detector unit in the overlapping region may correspond to a first pinhole and a second pinhole. In other words, the detector unit may detect photons from both the first pinhole and the second pinhole. A count and/or size of the detector units may be associated with a spatial resolution of the imaging device 400. In some embodiments, a count of the multiplexing channels may be less than or equal to a count of the sets of pinholes. For example, if the collimator 420 includes three sets of pinholes (e.g., a first set of pinholes, a second set of pinholes equipped with first filters, and a third set of pinholes equipped with second filters), for a dual-energy isotope trace, each detector unit in the detector 430 may have two channels. In some embodiments, a channel may correspond to an energy window corresponding to one of the one or more characteristic peaks of the radioactive tracer (or the channel may correspond to a characteristic peak of the radioactive tracer). The detector unit may classify projections of the photons into energy bins based on the energy window. For example, the detector unit may detect an energy of each photon, identify which energy window the energy of the photon belongs to, and add 1 to the cumulative count of photons in the channel corresponding to the energy window. For example, photons emitted by the radioactive tracer In-111 may be associated with two energy windows, e.g., a first energy window of [100-208) keV, and a second energy window of [208 keV, 300 keV]. For a specific photon with an energy of 200 keV, the detector unit may identify the energy of the specific photon is within the second energy window, and may add 1 to the cumulative count of photons in the channel corresponding to the second energy window.

Merely by way of example, for a radioactive tracer having two characteristic peaks, as shown in FIG. 4, the detector unit 435 may classify the detected photons (emitted by the radioactive tracer) based on two energy windows each of which corresponds to one of the two characteristic peaks. The characteristic peak may correspond to an energy. The detector unit 435 may detect photons from both a first pinhole (e.g., photons projected through a projection line corresponding to the auxiliary line 442) and a second pinhole (e.g., photons projected through a projection line corresponding to the auxiliary line 444), and generate first projection data associated with a first portion of photons each of which has a first energy, and second projection data associated with a second portion of photons each of which has a second energy. Then a first projection data set and a second projection data set measured by the plurality of detector units of the detector 430 may be acquired and be used to generate an image. More descriptions regarding image generation based on the first projection data set and the second projection data set may be found elsewhere in the present disclosure (e.g., FIG. 8 and the descriptions thereof).

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. In some embodiments, some other components/modules may be added into the imaging device 400. For example, the imaging device 400 may further include a first cover plate configured to adjustably cover the second set of second pinholes. The imaging device 400 may be switched between a working mode using the second set of second pinholes and another working mode without using the second set of second pinholes, by using the first cover plate (e.g., moving the first cover plate). In some embodiments, the first cover plate may be made of a material same as or different from the material of the collimator. For example, the material of the first cover plate may include a heavy metal such as lead and tungsten. As another example, the thickness of the first cover plate may relate to the energy of photons that the imaging system 100 is desired to detect. In some embodiments, the filters operably coupled to the collimator 420 may be replaced according to different needs.

FIG. 5A is a schematic diagram illustrating a cross-sectional view of a portion of an exemplary imaging device along a transaxial direction according to some embodiments of the present disclosure. FIG. 5B is a schematic diagram illustrating a cross-sectional view of an imaging device in FIG. 5A along an axial direction according to some embodiments of the present disclosure. The imaging device 500 may include a ring shaped collimator 510 and a ring shaped detector 520. In some embodiments, the imaging device 500 may further include a table (not shown) configured to support an object, a gantry (not shown) configured to support the collimator 510 and the detector 520, or the like.

As illustrated in FIG. 5A, the solid lines 512 may represent auxiliary lines corresponding to projection lines of a FOV through the first set of first pinholes, and the dashed lines 514 may represent auxiliary lines corresponding to projection lines of the FOV through the second set of second pinholes. According to FIG. 5A, the cross-sectional of the collimator 510 and the detector 520 along the transaxial direction (i.e., the x-axis direction in FIG. 1 of the imaging device 110) of the imaging device 500 are ring shaped. The detector 520 may be concentric with the collimator 510. The collimator 510 may include a first set of first pinholes (indicated by intersection points of the solid lines on the collimator 510) and a second set of pinholes (indicated by intersection points of the dashed lines on the collimator 510). Each second pinhole may be equipped with a filter (not shown).

The first set of first pinholes may be patterned such that first projections of a FOV of the imaging device 500 through the first set of first pinholes onto the detector 520 have no overlapping region. The first projections may cover the entire detector 520, see, solid lines 512 in FIGS. 5A and 5B. The second set of second pinholes may be patterned such that second projections of the FOV of the imaging device 500 through the second set of second pinholes onto the detector 520 have no overlapping region. The second projections may cover the entire detector 520, see, dashed lines 514 in FIGS. 5A and 5B. In such cases, by setting the first pinholes and the second pinholes to enable the first projections and the second projections to cover the entire detector 520, the sensitivity of the imaging device 500 may be improved. For example, the first set of first pinholes may include a first count of rows of first pinholes, and the second set of second pinholes may include a second count of rows of second pinholes. In some embodiments, each row of pinholes may be arranged on a plane perpendicular to the central axis of the collimator 510. In other words, each row of pinholes may be arranged in the transaxial direction (i.e., the x-direction in FIG. 1) of the imaging device 500. In some embodiments, each row of first pinholes may be (substantially) equally spaced, and each row of second pinholes may be (substantially) equally spaced. In some embodiments, spacings between a row of first pinholes may be equal to spacings between a row of second pinholes. More descriptions about a ring shaped collimator may be found elsewhere in the present disclosure (e.g., FIG. 6 and the descriptions thereof).

FIG. 6 is a schematic diagram illustrating an exemplary arrangement of pinholes of a ring shaped collimator according to some embodiments of the present disclosure. FIG. 6 is a front view of a ring shaped collimator (referred to as a collimator for brevity). As shown in FIG. 6, the collimator 600 (represented by the grey portion 640) may include a first set of first pinholes (indicated by trapezoids 610) and a second set of second pinholes (each second pinhole is obscured by a black rectangle 620 in FIG. 6). Each second pinhole may be equipped with a filter (indicated by the black rectangle) on the second pinhole. The second set of second pinholes may interleave between the first set of first pinholes. For example, the first set of first pinholes may include 7 rows of first pinholes indicated by dashed lines R1, R3, R5, R7, R9, R11, and R13, and the second set of second pinholes may include 6 rows of second pinholes indicated by dashed lines R2, R4, R6, R8, R10, and R12. Each row of pinholes may be arranged on a plane perpendicular to a central axis (i.e., the z-axis direction) of the collimator 600. The sizes of pinholes in each row may be the same. It should be noted that because only the filters are needed to cover the second pinholes, the sizes of the black rectangles in FIG. 6 do not necessarily indicate the sizes of the second pinholes. The sizes of graphs (i.e., trapezoids) representing the first pinholes may reflect the sizes of the first pinholes. When an FOV is located at the center of the ring shaped collimator 600, pinholes (first pinholes or second pinholes) are relatively close to the FOV, the sizes of the pinholes may be relatively small. For example, if an FOV is located at a position corresponding to row R7, sizes of first pinholes in row R7 may be smaller than sizes of first pinholes in row R1 or row R13. As another example, if an FOV is located at a position corresponding to row R7, sizes of second pinholes in row R6 may be smaller than sizes of second pinholes in row R2 or row R12. The pinholes in each row may be equally spaced. In some embodiments, a second row of first pinholes (e.g., row R3) may be offset by a certain angle with respect to a first row of first pinholes (e.g., row R1). In some embodiments, at least one second pinhole may be arranged at a center of a region encompassing four first pinholes. For example, a region 630 may encompass four first pinholes 612, 614, 616, and 618, and a second pinhole 622 may be located at the center of the region 630. In some embodiments, at least one first pinhole may be arranged at a center of a region encompassing four second pinholes. Accordingly, by setting the first set of first pinholes and the second set of second pinholes as illustrated in FIG. 6, a relatively large amount of photons can pass through the pinholes, thereby improving the sensitivity of an imaging device using the collimator 600.

Figure 7:
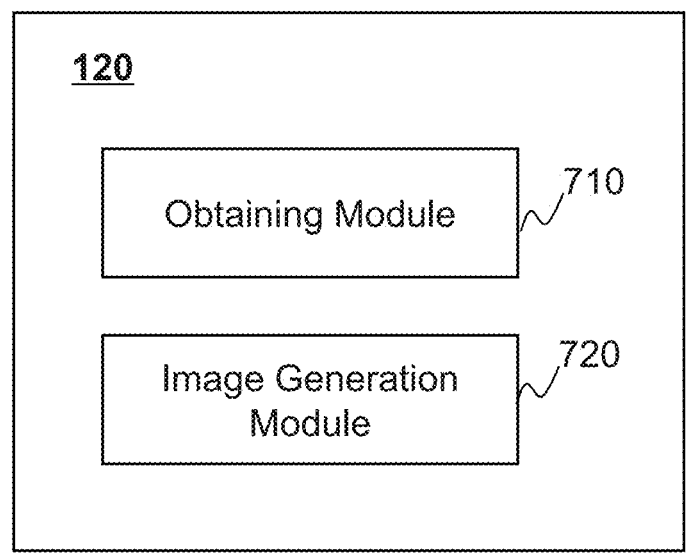
FIG. 7 is a block diagram illustrating an exemplary processing device according to some embodiments of the present disclosure.

FIG. 7 is a block diagram illustrating an exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 7, the processing device 120 may include an obtaining module 710 and an image generation module 720. Each of the modules described above may be a hardware circuit that is designed to perform certain actions, e.g., according to a set of instructions stored in one or more storage media, and/or any combination of the hardware circuit and the one or more storage media.

The obtaining module 710 may be configured to obtain data and/or information for image generation. For example, the obtaining module 710 may obtain a first projection data set associated with a first portion of photons each of which having a first energy. The obtaining module 710 may further obtain a second projection data set associated with a second portion of photons each of which having a second energy.

The image generation module 720 may be configured to generate an image based on the first projection data set and the second projection data set. In some embodiments, the image generation module 720 may determine a first piece of data corresponding to a first set of first pinholes and a second piece of data corresponding to a second set of second pinholes based on the first projection data set, the second projection data set, and a first matrix associated with the filters. The image generation module 720 may reconstruct the image based on the first piece of data and the second piece of data.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the obtaining module 710 may be divided into two units configured to obtain a first projection data set and a second projection data set, respectively. As another example, some other components/modules (e.g., a storage module) may be added into the processing device 120.

FIG. 8 is a schematic flowchart illustrating an exemplary process for generating an image according to some embodiments of the present disclosure. In some embodiments, process 800 may be implemented as a set of instructions (e.g., an application) stored in the storage device 130, storage 220, or storage 390. The processing device 120, the processor 210, and/or the CPU 340 may execute the set of instructions, and when executing the instructions, the processing device 120, the processor 210, and/or the CPU 340 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of the process 800 illustrated in FIG. 8 and described below is not intended to be limiting.

In 810, the processing device 120 (e.g., the obtaining module 710) may obtain a first projection data set associated with a first type of photons each of which has a first energy, and a second projection data set associated with a second type of photons each of which has a second energy. The first type of photons may also be referred to as the first portion of photons. The second type of photons may also be referred to as the second portion of photons. In some embodiments, the first projection data set and the second projection data set may be obtained from an imaging device (e.g., the imaging device 110), the storage device 130, or any other storage device. For example, the imaging device may transmit acquired first projection data set and/or second projection data set to the storage device 130, or any other storage device for storage. The processing device 120 may obtain the first projection data set and/or the second projection data set from the storage device 130, or any other storage device. As another example, the processing device 120 may obtain the first projection data set and the second projection data set from the imaging device directly.

In some embodiments, the first projection data set and the second projection data set may be acquired by the imaging device (e.g., a SPECT device) in a predetermined time period after a radioactive tracer having two characteristic peaks is injected into an object. For instance, the predetermined time period after the injection of the radioactive tracer may be 1 minute-2 minutes, or 1.5 minutes-2 minutes, or 1 minute-3 minutes, etc., after the injection of the radioactive tracer. As another example, the first projection data set and the second projection data set may be acquired by the imaging device in a certain time period after the tracer distribution in the object reaches equilibrium or steady-state. The first energy and the second energy may correspond to the two characteristic peaks of the radioactive tracer, respectively. In some embodiments, the radioactive tracer may include two single-energy isotope tracers (e.g., Tc-99 and F-18) or a dual-energy isotope tracer (i.e., having two characteristic peaks, for example, In-111). More descriptions regarding the radioactive tracer may be found elsewhere in the present disclosure (e.g., FIG. 4 and the descriptions thereof).

During a process for acquiring the first projection data set and the second projection data set by the imaging device, photons (including the first portion of photons and the second portion of photons) may be collimated by a collimator of the imaging device. The collimator may be a multi-pinhole collimator having a first set of first pinholes and a second set of second pinholes. Each second pinhole of the second set of second pinholes may be equipped with a filter. More descriptions regarding the collimator may be found elsewhere in the present disclosure (e.g., FIG. 4, FIG. 5A, and FIG. 5B and the descriptions thereof).

The first projection data set may include a plurality of first sub-sets of data each of which is measured by one of a plurality of detector units of a detector of the imaging device. The second projection data set may include a plurality of second sub-sets of data each of which is measured by one of the plurality of detector units. Each first sub-set of data may correspond to one second sub-set of data. As used herein, one first sub-set of data corresponding to one second sub-set of data may refer that both the first sub-set of data and the second sub-set of data are measured by a same detector unit. For one first sub-set of data and a corresponding second sub-set of data, the first sub-set of data measured by a detector unit may be associated with a total count of photons with the first energy passing through a corresponding first pinhole and a corresponding second pinhole. Similarly, each second sub-set of data measured by the detector unit may be associated with a total count of photons with the second energy passing through the corresponding first pinhole and the corresponding second pinhole. A first ratio of a count of photons with the first energy passing through the first pinhole to a count of photons with the second energy passing through the first pinhole may be different from a second ratio of a count of photons with the first energy passing through the second pinhole to a count of photons with the second energy passing through the second pinhole. The processing device 120 may generate an image based on the difference between the first ratio and the second ratio.

In 820, the processing device 120 (e.g., the image generation module 720) may generate an image based on the first projection data set and the second projection data set. In some embodiments, the processing device 120 may generate the image using a reconstruction algorithm. Exemplary reconstruction algorithms may include a maximum likelihood expectation maximization (MLEM) algorithm, an algebraic reconstruction technique (ART), a simultaneous algebraic reconstruction technique (SART), or the like, or any combination thereof.

In some embodiments, the processing device 120 may determine a first piece of data corresponding to the first set of first pinholes and a second piece of data corresponding to the second set of second pinholes based on the first projection data set, the second projection data set, and a first matrix associated with the filters. The first piece of data may be associated with a first count of photons, among the first portion of photons and the second portion of photons, that pass through the first set of first pinholes. The second piece of data may be associated with a second count of photons, among the first portion of the photons and the second portion of the photons, that pass through the second set of second pinholes. In some embodiments, the first matrix may be associated with transmissivities of the photons having the first energy and the photons having the second energy passing through the filters. In some embodiments, the first matrix may be further associated with yield abundances of the radioactive tracer at the first energy and the second energy. The processing device 120 may reconstruct the image based on the first piece of data and the second piece of data. For example, the processing device 120 may reconstruct the image based on the first piece of data and the second piece of data using the MLEM algorithm.

According to some embodiments of the present disclosure, for a radioactive tracer having two characteristic peaks, the processing device 120 may determine the first piece of data and the second piece of data according to Equation (1):

$$\begin{bmatrix} y_L \\ y_H \end{bmatrix} = \begin{bmatrix} a_L & f_L a_L \\ a_H & f_H a_H \end{bmatrix} \begin{bmatrix} l_1 \\ l_2 \end{bmatrix}, \quad (1)$$

where $y_H$ denotes the first projection data set; $y_L$ denotes the second projection data set; $\alpha_H$ and $\alpha_L$ denote yield abundances of the radiative tracer at the first energy (e.g., a relatively high energy) and the second energy (e.g., a relatively low energy), respectively; $f_H$ and $f_L$ denote transmissivities of the photons having the first energy and the photons having the second energy passing through the filters; $l_1$ denotes the first piece of data associated with the first set of first pinholes; and $l_2$ denotes the second piece of data associated with the second set of second pinholes. In some embodiments, $$\begin{bmatrix} a_L & f_L a_L \\ a_H & f_H a_H \end{bmatrix}$$

may denote the first matrix associated with the filters.

Alternatively, in some embodiments, the processing device 120 may determine the image at least based on a second matrix including a first sub-matrix associated with the first set of first pinholes and a second sub-matrix associated with the second set of second pinholes. In some embodiments, the second matrix may also be referred to as a system matrix associated with the acquisition of the first projection data set and the second projection data set. The system matrix may describe or correspond to the physical geometry of one or more components (e.g., the collimator, the detector, the first set of first pinholes, and the second set of second pinholes) of the imaging device with respect to the FOV. Exemplary parameters associated with the physical geometry of the one or more components may include a size of the collimator (e.g., a radius of a transaxial section of a cylindrical collimator, an area of a collimator plate), a position of the collimator (or a relative position with respect to the detector), positions of pinholes (including the first pinholes and the second pinholes) on the collimator, a size of the detector, a position of the detector (or a relative position with respect to the collimator), a size of each detector unit of the detector, a detection efficiency of the detector, a size of the FOV, or the like, or any combination thereof. The first sub-matrix associated with the first set of first pinholes may refer to a first system matrix of an imaging system without the second set of second pinholes. Similarly, the second sub-matrix associated with the second set of second pinholes may refer to a second system matrix of an imaging system without the first set of first pinholes. Merely by way of example, the processing device 120 may determine the image based on Equation (2) as follows:

$$\begin{bmatrix} y_L \\ y_H \end{bmatrix} = \begin{bmatrix} a_L & f_L a_L \\ a_H & f_H a_H \end{bmatrix} \begin{bmatrix} G_1 \\ G_2 \end{bmatrix} x, \quad (2)$$

where $G_1$ denotes the first sub-matrix associated with the first set of first pinholes; $G_2$ denotes the second sub-matrix associated with the second set of second pinholes; and x denotes the image.

In some embodiments, the first sub-matrix and/or the second sub-matrix may be determined based on a calibration technique for calibrating the imaging device. For example, for determining the first sub-matrix, a plurality of first point spread functions (PSFs) of points at different positions in the FOV of the imaging device may be determined when the second set of second pinholes are covered using a second cover plate. In some embodiments, the first PSFs may be obtained, e.g., by performing a simulation for the imaging device without the second set of second pinholes. The second cover plate may be configured to prohibit photons from passing through the second pinholes. In some embodiments, the second cover plate may be the same or different as the first cover plate described in FIG. 4. The first sub-matrix may be determined based on the plurality of first PSFs according to, e.g., a convolution algorithm. Similarly, for determining the second sub-matrix, a plurality of second point spread functions (PSFs) of points at different positions in the FOV of the imaging device may be determined when the first set of first pinholes are covered using a cover plate (e.g., the second cover plate). The second sub-matrix may be determined based on the plurality of second PSFs.

In some embodiments, the first sub-matrix and/or the second sub-matrix may be determined based on a simulation technique. For example, for determining the first sub-matrix, the processing device 120 may obtain a first simulation image generated assuming that the collimator only has the first set of first pinholes (or the second set of second pinholes are covered using the second cover plate). The first simulation image may include a plurality of pixels each of which corresponds to a detector unit. The processing device 120 may determine simulation projection data corresponding to each of the plurality of pixels. The processing device 120 may determine the first sub-matrix based on the simulation projection data. Similarly, for determining the second sub-matrix, the processing device 120 may obtain a second simulation image generated assuming that the collimator only has the second set of second pinholes (or the first set of first pinholes are covered using the second cover plate). The second simulation image may include a plurality of pixels each of which corresponds to a detector unit. The processing device 120 may determine simulation projection data corresponding to each of the plurality of pixels. The processing device 120 may determine the second sub-matrix based on the simulation projection data.

In some embodiments, in order to meet different requirements (e.g., relatively high sensitivity but low resolution), the imaging device used to acquire the first projection data set and the second projection data set may be optimized to obtain an updated first projection data set and an updated second projection data set. An updated image that satisfies the requirements may be generated based on the updated first projection data set and the updated second projection data set. Generally, on one hand, the sensitivity of the imaging device may be associated with a thickness of the filter. For example, when considering a filter made of a specific material, the sensitivity of the imaging device may be decreased with the increased thickness of the filter. The sensitivity of the imaging device may be evaluated based on Equations (3-5) as follows:

$$S_{inc}(t) = \frac{f_L a_L G_2 x + f_H a_H G_2 x}{a_L G_1 x + a_H G_1 x}, \quad (3)$$

$$f_L = \exp(-\mu_L t), \quad (4)$$

$$f_H = \exp(-\mu_H t), \quad (5)$$

where $S_{inc}(t)$ denotes the sensitivity of the imaging device; $\mu_H$ and $\mu_L$ denote linear attenuation coefficients of the specific material at the first energy and the second energy, respectively; and t denotes the thickness of the filter. On the other hand, the spatial resolution of the imaging device may be associated with the thickness of the filter. For example, when considering a filter made of the specific material, the spatial resolution of the imaging device may be improved with the increased or decreased thickness of the filter. The spatial resolution of the imaging device may be evaluated based on a condition number of the first matrix associated with the filters. The condition number of the first matrix may be described in Equations (6) as follows:

$$C(t) = Cond\left(\begin{bmatrix} a_L & f_L(t)a_L \\ a_H & f_H(t)a_H \end{bmatrix}\right), \quad (6)$$

where $C(t)$ denotes a condition number of the first matrix. The trade-off between the sensitivity and the spatial resolution of the imaging device may be leveraged with different filtration design (e.g., different thicknesses, different materials of the filter).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, during the process for generating the image, the projection data including the first projection data set and the second projection data set may be corrected based on an anatomical image acquired by another imaging device (e.g., a CT device). As another example, one or more other optional operations (e.g., a storing operation) may be added elsewhere in the process 800. In the storing operation, the processing device 120 may store information and/or data (e.g., the first projection data set, the second projection data set, the first matrix, the second matrix (or the system matrix), etc.) associated with the imaging system 100 in a storage device (e.g., the storage device 130) disclosed elsewhere in the present disclosure.

FIG. 9A illustrates a cross-sectional view of a phantom according to some embodiments of the present disclosure. A phantom 900 may include six groups of rods of different diameters including 0.5 mm, 0.6 mm, 0.8 mm, 1 mm, 1.2 mm, and 1.5 mm. The six groups of rods may be set to have different resolutions. Each rod may be simulated to have an activity equivalent to the radiation of a radioactive tracer (e.g., In-111). The activity of each rod to background (e.g., a region 910) may be 4:1.

FIGS. 9B and 9C illustrate images of the phantom 900 in FIG. 9A according to some embodiments of the present disclosure. Image 900b in FIG. 9B is a cross-sectional view along an axial direction of the phantom 900, and image 900c in FIG. 9C is a cross-sectional view along the direction of CC' of the rods with sizes 0.8 mm to 1.2 mm. Images 900b and 900c may be acquired by scanning the phantom 900 with 300 seconds using a SPECT device having a spectral multiplexing collimator described in the present disclosure. The spectral multiplexing collimator may have a first set of first pinholes and a second set of second pinholes. Each second pinhole may be equipped with a tungsten filter with a thickness of 0.1 mm.

FIGS. 9D and 9E illustrate images of the phantom 900 in FIG. 9A according to some embodiments of the present disclosure. Image 900d in FIG. 9D is a cross-sectional view along an axial direction of the phantom 900, and image 900e in FIG. 9E is a cross-sectional view along the direction of DD' of the rods with sizes 0.8 mm to 1.2 mm. Images 900d and 900e may be acquired by scanning the phantom 900 with 300 seconds using a SPECT device having a single-set collimator. Compared with the spectral multiplexing collimator used in acquiring images 900b and 900c, the single-set collimator may only have the first set of first pinholes.

According to the comparison between images 900b and 900d, and the comparison between images 900c and 900e, the images acquired using the spectral multiplexing collimator may have improved image resolution (e.g., see rods with size 0.8 mm in images 900b and 900c), superior contrast recovery, lower noise, and lower aliasing artifacts. As a result, using the spectral multiplexing collimator, a higher contrast to noise ratio may be achieved, or the same contrast to noise ratio with a shorter acquisition time may be achieved. The improved angular sampling may be beneficial to improve spatial resolution and reduce aliasing artifacts.

Figure 10A:
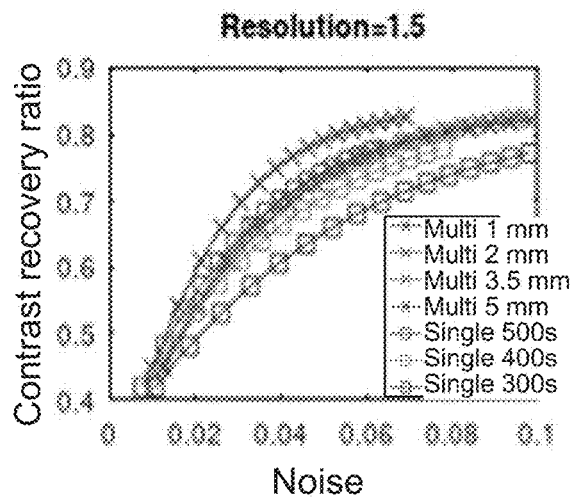
FIGS. 10A to 10D are graphs illustrating curves of contrast recovery ratio to noise at different resolution levels according to some embodiments of the present disclosure.
Figure 10B:
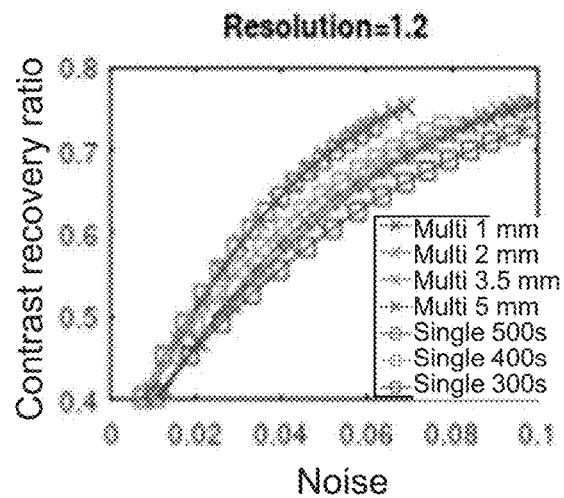
Figure 10C:
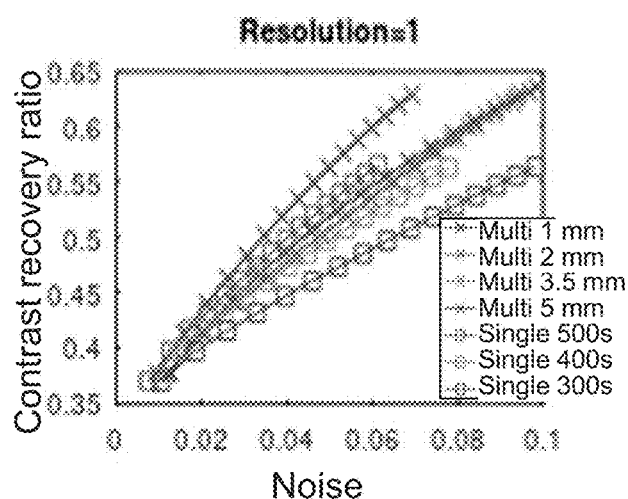
Figure 10D:
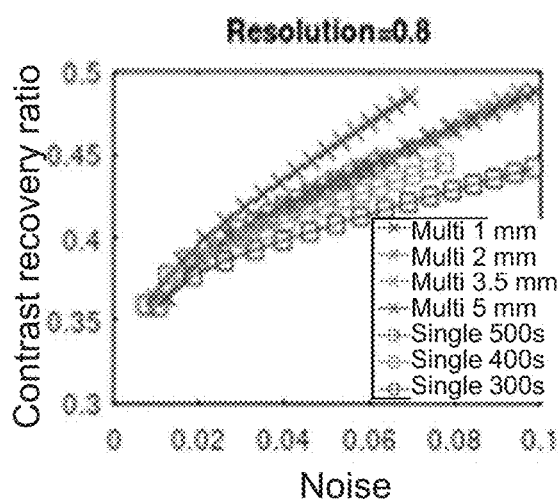

FIGS. 10A to 10D are graphs illustrating curves of contrast recovery ratio to noise at different resolution levels according to some embodiments of the present disclosure. As used herein, a contrast recovery ratio (CR) refers to a ratio of a reconstructed contrast to a true contrast. FIG. 10A shows a graph of curves of contrast recovery ratio to noise at a resolution of 1.5. FIG. 10B shows a graph of curves of contrast recovery ratio to noise at a resolution of 1.2. FIG. 10C shows a graph of curves of contrast recovery ratio to noise at a resolution of 1. FIG. 10D shows a graph of curves of contrast recovery ratio to noise at a resolution of 0.8. In FIGS. 10A to 10D, curves associated with using a single-set collimator (also be referred to as Single for brevity) may be obtained based on different acquisition times (or different scan times) by using a same single-set collimator having only a first set of first pinholes. Curves associated with using a spectral multiplexing collimator (also be referred to as Multi for brevity) may be obtained based on an acquisition time of 300 seconds by using a spectral multiplexing collimator equipped with filters with different thicknesses. The spectral multiplexing collimator may include the first set of first pinholes and an additional set of second pinholes. A filter may be disposed on each second pinhole. The filter may be a tungsten filter.

According to FIGS. 10A to 10D, at the same resolution and noise levels, the longer the acquisition time is, the greater the CR may be achieved by using the single-set collimator. At the same resolution and noise levels, the less the thickness of the filter is, the greater the CR may be achieved by using the spectral multiplexing collimator. At the same resolution and contrast levels, 300 seconds scan using the spectral multiplexing collimator with 0.1 mm thick filters may achieve improved or equivalent noise reduction compared with the 500 seconds scan using the single-set collimator. At the same resolution and noise levels, 300 seconds scan using the spectral multiplexing collimator with 0.1 mm thick tungsten filter may achieve greater or equivalent CR than the 500 seconds scan using the single-set collimator. This allows for at least 40% time-saving in acquisition protocol design.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A single-photon emission computed tomography (SPECT) system, comprising:
    a detector configured to detect photons; and
    a collimator having at least two sets of pinholes, the at least two sets of pinholes including a first set of first pinholes and a second set of second pinholes, wherein each second pinhole of the second set of second pinholes is equipped with a filter configured to filter the photons, the first set of first pinholes and the second set of second pinholes being arranged on a same plane of the collimator.

2. The SPECT system of claim 1, wherein
    the first set of first pinholes are patterned such that first projections of a field of view (FOV) of the SPECT system through the first set of first pinholes onto the detector have no overlapping region;
    the second set of second pinholes are patterned such that second projections of the FOV of the SPECT system through the second set of second pinholes onto the detector have no overlapping region; and
    at least one of the first projections is overlapped with at least one of the second projections.

3. The SPECT system of claim 2, wherein at least one of the first projections is overlapped with at least two of the second projections or at least one of the second projections is overlapped with at least two of the first projections.

4. The SPECT system of claim 3, wherein the second set of second pinholes interleaves between the first set of first pinholes.

5. The SPECT system of claim 4, wherein the first set of first pinholes includes a first count of rows of first pinholes, and the second set of second pinholes includes a second count of rows of second pinholes, the second count being less than the first count.

6. The SPECT system of claim 5, wherein at least one second pinhole of the second set of pinholes is arranged at a center of a region encompassing four first pinholes adjacent to the at least one second pinhole.

7. The SPECT system of claim 6, wherein
    the collimator is ring shaped;
    each row of first pinholes is arranged on a plane perpendicular to a central axis of the collimator;
    each row of second pinholes is arranged on a plane perpendicular to the central axis of the collimator; and
    the detector is ring shaped and is concentric with the collimator.

8. The SPECT system of claim 7, wherein each row of first pinholes are equally spaced, or each row of second pinholes are equally spaced.

9. The SPECT system of claim 8, wherein spacings between the each row of first pinholes are equal to spacings between the each row of second pinholes.

10. The SPECT system of claim 1, wherein the photons are emitted from an object with a radioactive tracer, the radioactive tracer having at least two characteristic peaks.

11. The SPECT system of claim 10, wherein the detector is configured for multiplex detection of a first portion of the photons each of which having a first energy, and a second portion of the photons each of which having a second energy, the first energy and the second energy corresponding to two of the at least two characteristic peaks, respectively.

12. The SPECT system of claim 11, wherein
    the photons detected by the detector include a first count of photons that pass through the first set of first pinholes, and a second count of photons that pass through the second set of second pinholes;
    the first count of photons include a plurality of first photons each of which having the first energy and a plurality of second photons each of which having the second energy;
    the second count of photons include a plurality of third photons each of which having the first energy and a plurality of fourth photons each of which having the second energy; and
    a first ratio of a count of the first photons to a count of the second photons is different from a second ratio of a count of the third photons to a count of the fourth photons.

13. The SPECT system of claim 10, wherein the radioactive tracer includes at least one of indium-111, or iodine-131.

14. The SPECT system of claim 1, wherein the filter includes a heavy metal sheet.

15. The SPECT system of claim 14, wherein the filter has a thickness in a range from 0.01 mm to 1 mm.

16. The SPECT system of claim 1, wherein the collimator further includes a cover plate configured to adjustably cover the second set of second pinholes.

17. The SPECT system of claim 1, wherein each first pinhole of the first set of first pinholes is equipped with a filter different from the filter that equipped on each second pinhole of the second set of second pinholes.

18. The SPECT system of claim 1, wherein the first set of first pinholes are equipped with no filter or equipped with a second filter different from the filter of the second set of second pinholes.

19. A system, comprising:
    at least one storage device storing executable instructions for single-photon emission computed tomography (SPECT) imaging; and
    at least one processor in communication with the at least one storage device, wherein when executing the executable instructions, the at least one processor is configured to cause the system to perform operations including:
        obtaining a first projection data set associated with a first portion of photons each of which having a first energy, and a second projection data set associated with a second portion of photons each of which having a second energy, wherein the first portion of photons and the second portion of photons are collimated by a first set of first pinholes and a second set of second pinholes of a collimator of a SPECT device, each second pinhole of the second set of second pinholes being equipped with a filter, the first set of first pinholes and the second set of second pinholes being arranged on a same plane of the collimator; and generating an image based on the first projection data set and the second projection data set.

20. A collimator for single-photon emission computed tomography (SPECT) imaging comprising:

a first set of first pinholes; and a second set of second pinholes, wherein each second pinhole of the second set of second pinholes is equipped with a filter configured to filter photons, the first set of first pinholes and the second set of second pinholes being arranged on a same plane of the collimator.

* * * * *